United States Patent
Werner

(10) Patent No.: US 6,309,344 B1
(45) Date of Patent: Oct. 30, 2001

(54) MALE ERECTION ENHANCER AND SUSTAINER

(76) Inventor: Glen F. Werner, 386 Saunders St., Murray, UT (US) 84107

( * ) Notice: Subject to any disclaimer, the term of this patent is extended or adjusted under 35 U.S.C. 154(b) by 0 days.

(21) Appl. No.: 09/545,799

(22) Filed: Apr. 8, 2000

(51) Int. Cl.$^7$ ........................................... A61F 5/00
(52) U.S. Cl. ............................................... 600/41
(58) Field of Search .................. 600/39–42; 128/897, 128/898

(56) References Cited

U.S. PATENT DOCUMENTS

| | | | |
|---|---|---|---|
| 3,636,948 | * | 1/1972 | Atchley ................................... 600/39 |
| 3,773,040 | * | 11/1973 | Gavrilovich ........................... 600/39 |
| 5,063,915 | * | 11/1991 | Wyckoff ................................. 600/39 |
| 5,085,209 | * | 2/1992 | Gottschalk ............................. 600/41 |
| 5,221,251 | * | 6/1993 | Edminster ............................. 600/41 |
| 6,015,379 | * | 1/2000 | Sachse ................................... 600/39 |

* cited by examiner

Primary Examiner—Samuel G. Gilbert

(57) ABSTRACT

A penile erection enhancing and sustaining device is for assisting in obtaining and maintaining an erection for men suffering with ED. This inexpensive constrictor can be quickly applied, easily adjusted and instantaneously released when desired. It is used to restrain the flow of blood from the penis during copulation. A Velcro® hook and loop fastener of sufficient length attached on opposite ends of a broad rubber strip adapts the constrictor to varying penis sizes. The broadness of the constrictor avoids the localized pressure caused by narrow rings and compresses and decreases the interior volume of erectile tissue within the penis thus increasing the pressure of the available blood. The preferred positioning the broad rubber strip is to encircle the penis at its base between the testicle and the body providing firm positioning and makes it relatively inconspicuous and unlikely to come in contact with the partner. The quick release permits unrestricted ejaculation, and to avoid disruption of concentration of the act, removal at the time of release is not necessary. The long lasting materials of the constrictor are hypoallergenic and washable with unlimited reusability. It can be used in conjunction with the vacuum pump, substituting it for the narrow rings that are not releasable, and can also be used in conjunction with Viagra® users when the one-hour waiting period is inconvenient. There is no need for expensive doctor appointments, surgery, shots, pills, or prescriptions.

1 Claim, 1 Drawing Sheet

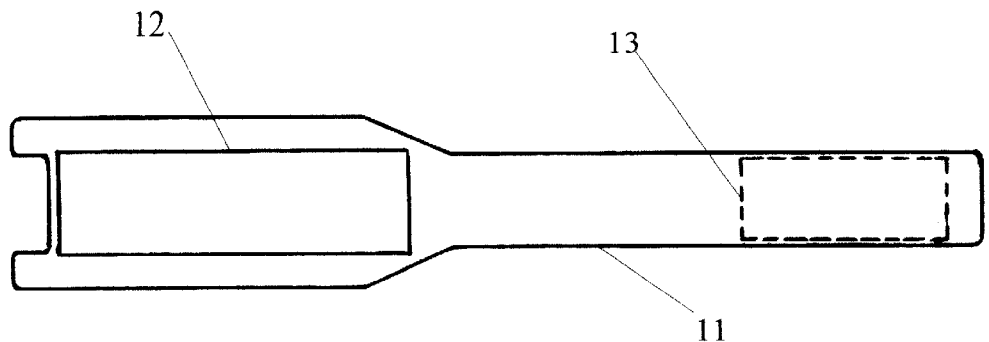
Fig. 1
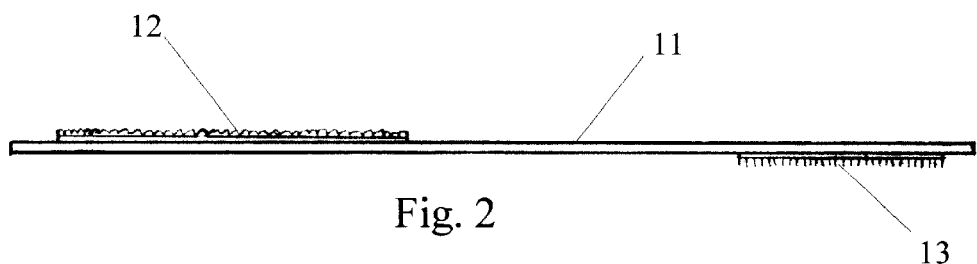
Fig. 2
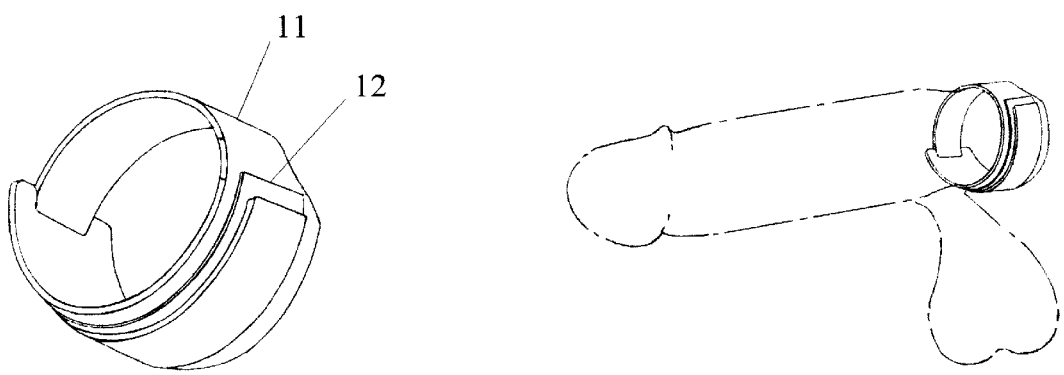
Fig. 3
Fig. 4

MALE ERECTION ENHANCER AND SUSTAINER

BACKGROUND—FIELD OF INVENTION

This invention is an inexpensive solution for men suffering with all types of Erectile Dysfunction (ED), who can achieve at least a partial erection or who cannot maintain an erection, and it consists simply of a broad rubber strip with a Velcro® hook and loop type connector for easy connection and quick release.

BACKGROUND—DESCRIPTION OF PRIOR ART

Erectile Dysfunction (or impotency) is a depressing and traumatizing psychological and/or physiological disorder which can affect men of any age and can be a source of marital discord.

As is well known, erection occurs under sexual stimulation, which causes the lengthwise sponge like tissues of the penis to become engorged with blood, and as long as this condition prevails, the erection is maintained. However, in some individuals suffering from physical and/or psychological impotence, the state of erection is not firm enough or not maintained long enough to complete copulation satisfactorily for both partners. Many devices, pills, and medical treatments have been developed to treat ED.

Several medical remedies and devices are available to treat ED, each having notable disadvantages:

(a) The penile implant medical procedure denies the patient the ability to achieve a normal erection after this extremely expensive invasive procedure.

(b) The penile injection with a hypodermic needle is not only painful and traumatizing but also could lead to infection, irritation, or soreness.

(c) The vacuum pump, at about $200, is used to draw blood into the penis, which uses a molded rubber ring as a constraint to resist the out flow of blood, is ineffective because when the vacuum is released partial shrinkage takes place.

(d) The vacuum pump, with its kit of various size constriction rings, requires several minutes to apply with considerable disruption of arousal. Partial penile shrinkage takes place after releasing the vacuum resulting in a lack of the sensitivity necessary for sexual satisfaction. The constriction rings produce localizes pressure, or pinching, because of their narrow cross section. This pressure is not only uncomfortable but can cause irritation or damage to the veins in the penis. The removal of the ring can be quite uncomfortable and neither release nor removal can be accomplished during lovemaking, which obviously would also restrict of the flow of semen.

(e) Viagra®, which requires a doctor's appointment for a very expensive prescription that may have medical side effects, requires a waiting period of about an hour after taking each pill. Some men have reported falling asleep waiting for the pill to take effect, wasting about $10 at today's prices. Many prescribed medications can cause decreased sex drive, impotence, or difficulty having an orgasm and the taking of still another pill (Viagra®) may cause additional side effects and can even be deadly if drugs containing nitrates are being used by that person.

OBJECTS AND ADVANTAGES

This invention, a penile erection enhancer and sustainer, evolved from the realization that a broad rubber strip looped snugly around the penis with the ends joined by attached Velcro® hook and loop strips could be used as an excellent constriction. Accordingly, several objects and advantages of this invention are:

(a) to provide a broad constriction that restricts the flow of blood from the penis resulting in a sustained erection without the discomfort of localized pressure, or pinching, inflicted by a narrow constraint;

(b) to provide a broad constriction that is simple in design and inexpensive;

(c) to provide a broad constricting band that is flexible and elastic that can be joined at the ends by hook and loop pile attachment to form a constricting loop;

(d) to provide a broad constriction that encircles the base of the penis and scrotum at the junction of the pubis, which is easily connected, adjustable to size and comfort, and is easily and quickly releasable and/or removable;

(e) to provide a broad constriction that can constrict the penis thereby reducing the interior volume of its erectile tissue that in turn increases the pressure of the available blood within the penis, which increases its firmness thereby increases its sensitivity which is necessary for sexual satisfaction;

(f) to provide a broad constriction that can be readily positioned and/or adjusted on the penis in the dark or under the bed covers;

(g) to provide a broad constriction that can be quickly released at any time and especially just before ejaculation;

(h) to provide a broad adjustable constrictor that can be used in conjunction with the vacuum pump instead of the narrow solid rings which are neither adjustable, releasable nor easy to remove;

(i) to provide a broad constricting device that does not require a doctor appointment, medical procedure, nor an expensive prescription;

(j) to provide a broad constriction that can be used spontaneously when the mood dictates rather than a lengthy waiting period as Viagra® requires;

(k) to provide a broad constriction that can be used in conjunction with Viagra® as a good substitute for users who sometimes find the one hour waiting period inconvenient when the mood spontaneously dictated;

(l) to provide a broad constriction with the recommendation of positioning it at the base of the penis and encircling the penis and scrotum at the junction of the pubis;

(m) to provide a broad constriction that when placed in the recommended position is nearly unnoticeable by the partner;

(n) to provide a broad constriction that when placed in the recommended position is extremely unlikely to come in contact with the partner;

(o) to provide a broad constriction that is hand washable or could be included in a normal load of laundry;

(p) to provide a broad constriction composed of non-allergenic materials;

(q) to provide a broad constriction that is reusable;

(r) to provide a broad constriction that can fit conveniently in the smallest of spaces in luggage, when traveling, without the need of a special container or wrapping.

Further objects and advantages will become apparent from a consideration of the ensuing description and drawings.

DRAWING FIGURES

FIG. 1 is a plan view showing the shape of the rubber strip, broader at one end with the small-extended centering tabs, and the positioning of the hook and loop (Velcro® hook and loop) connector parts.

FIG. 2 is a side view of the thin rubber strip showing the positioning of the hook and loop connector parts.

FIG. 3 is a perspective showing the ends of the constrictor joined by means of the hook and loop connector parts engaged to form the constriction loop.

FIG. 4 is a side view showing the positioning of the constrictor on the penis in relation to the testicles.

DESCRIPTION—FIGS. 1 TO 4

The constrictor, FIGS. 1 and 2, is composed of only three parts. Member 11 is a strip of thin pure gum rubber, approximately 0.06 inches thick, of sufficient length, approximately 6½ inches, to wrap around the penis and scrotum and overlap at the ends for connection to form a loop. The broadness at the one end of the thin strip was designed as a gripping surface. This broadness extends to the end of the strip and is notched to form two centering tabs that were designed to facilitate connection of the ends of the strip to form a uniform loop. Member 12 is Velcro® hook and loop fabric attached to the broad end of member 11 and is of sufficient length and width to receive connecting member 13 to form variable loop sizes. Member 13 is Velcro® hook and loop hook fabric smaller in width and length than member 12, to avoid exposure of the hook fabric when joined, and is attached to the narrow end of the rubber strip but on the opposite side from member 12. The centering tabs were found to be desirable because the connection of the Velcro® hook and loop parts should be able to be made in darkness by feel alone, and the best connection is accomplished by good alignment of the two Velcro® hook and loop components to form a uniform loop. The preferred method of attaching the Velcro® hook and loop to the rubber strip is by sewing but heat or chemical bonding could be alternate methods.

SUMMARY, RAMIFICATIONS, AND SCOPE

Accordingly, the principal objective of the erection enhancer and sustainer (broad constrictor) is to restrict the flow of blood from the penis when encircled by it but has many advantages over prior art. Pressure resulting from the broadness of the constrictor reduces the volume of erectile tissue within the penis thus increasing the pressure of the available blood, thereby enhancing the firmness of the erection. (Since the application of the constrictor forces the blood in both directions within the penis it is logical then to force the blood from the root of the penis through the constriction to its shaft with gentle but firm finger pumping strokes to further enhance its firmness, if desired. This procedure can be called U-pump for you, the participant, do the pumping relating it to a vacuum pump.) The positioning of the constrictor at the base of the penis between the testicles and the body has the advantages of keeping it in place without the need for tape, mostly hidden from the partner, out of contact with the partner, and allowing the full length of the penis to be engorged with blood. The materials of the constrictor, to which the skin is not allergic, are flexible, and washable making the constrictor reusable. The constrictor can be used in conjunction with the vacuum pump, in place of the solid rings, providing a broader constriction that does not produce the localized pressure (or pinching) of a narrow cross section, is quickly and easily adjustable to size, is releasable even during copulation, and is easy to remove without discomfort. The constrictor can also be used in conjunction with the pill. Viagra® works well for those who can tolerate it, but for those unanticipated spontaneous moments when the pill was not taken in advance and a one-hour waiting period is not convenient or possible the constrictor can be used as an excellent substitute or back up.

What is claimed is:

1. A constriction loop device for enhancing and sustaining an erection of the penis comprising a single band of pure gum rubber including a broad gripping portion and strap portion the broad gripping portion having centering tabs formed by notching an end portion of the broad gripping portion, the opposite end of the broad gripping portion narrowing to form a strap of sufficient length to encircle the base of the penis and scrotum at the junction of the pubis, the strap having attached interlocking hook material adapted to overlap the broad gripping portion and being guided between the centering tabs adapted to be connected to an attaching portion of loop interlocking material which is located on the opposite side of the broad gripping portion from the interlocking hook material to form the constriction loop, wherein the broad gripping portion of the constriction loop is designed as a gripping surface allowing it to be held while the strap portion is stretched to form the constriction loop.

* * * * *